United States Patent [19]

Ueda et al.

[11] Patent Number: 4,686,227
[45] Date of Patent: Aug. 11, 1987

[54] IMIDAZOISOQUINOLINE COMPOUNDS USEFUL AS ANTI-ULCERATIVE AGENTS

[75] Inventors: Ikuo Ueda, Uenohigashi; Youichi Shiokawa, Hozumidai; Masayuki Kato, Minoo; Nobukiyo Konishi, Aotanai; Atsushi Akahane, Midorigaoka, all of Japan

[73] Assignee: Fujisawa Pharmaceutical Co., Ltd., Osaka, Japan

[21] Appl. No.: 745,638

[22] Filed: Jun. 17, 1985

[30] Foreign Application Priority Data

Jun. 18, 1984 [GB] United Kingdom ............ 8415540

[51] Int. Cl.$^4$ ............ A61K 31/395; C07D 471/04; C07D 405/04
[52] U.S. Cl. ............ 514/292; 546/84; 544/179; 544/215; 544/361; 544/126
[58] Field of Search ............ 546/84

[56] References Cited

U.S. PATENT DOCUMENTS 4,075,342  2/1976  Sale et al. ............ 546/84

OTHER PUBLICATIONS

Chemical Abstracts, 102(9):78780y.
Kobayashi et al., Heterocycles, vol. 15, No. 2, 1981, pp. 1223 to 1225.
Yamanaka et al., Chem. Pharm. Bull., vol. 27, (4) (1979), pp. 1004 to 1008.

Primary Examiner—Henry R. Jiles
Assistant Examiner—J. Richter
Attorney, Agent, or Firm—Jordan B. Bierman

[57]  ABSTRACT

A compound of the formula:

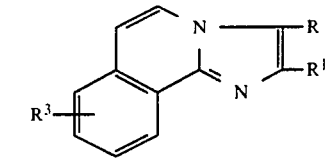

wherein
$R^1$ is lower alkyl,
$R^3$ is hydrogen, halogen or ar(lower)alkoxy, and
R is lower alkanoyl, nitroso, amino, carboxy, esterified carboxy, carbamoyl, hydroxycarbamoyl, haloformyl, aminomethyleneamino which may be substituted with cyano or lower alkyl, iminomethylamino which may be substituted with cyano or lower alkyl, or a group of the formula: —A—$R^2$ in which
A is lower alkylene and
$R^2$ is di(lower)alkylamino, cyano, lower alkoxy, N-containing heterocyclic group which may have suitable substituent(s), lower alkynyloxy, lower alkenyloxy, lower alkylthio, amino(lower)alkylthio, lower alkylsulfinyl, lower alkylsulfonyl, carboxy, esterified carboxy, carbamoyl, hydroxycarbamoyl, hydroxy, lower alkanoyloxy, heterocyclicamino (lower)alkylthio having two oxo groups, hydrogen or a group of the formula:

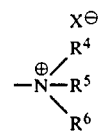

in which
$R^4$, $R^5$ and $R^6$ are each lower alkyl and
X is an acid residue,
and pharmaceutically acceptable salts thereof.

The compounds are useful as anti ulcer agents.

9 Claims, No Drawings

IMIDAZOISOQUINOLINE COMPOUNDS USEFUL AS ANTI-ULCERATIVE AGENTS

The present invention relates to novel imidazoisoquinoline compounds and pharmaceutically acceptable salt thereof. More particularly, it relates to novel imidazoisoquinoline compounds and pharmaceutically acceptable salts thereof which have inhibitory activity on ulcer, to processes for preparation thereof, to pharmaceutical composition comprising the same, and to method of using the same therapeutically in the treatment of ulcer in human being and animals.

Accordingly, one object of this invention is to provide novel imidazoisoquinoline compounds and pharmaceutically acceptable salt thereof, which are useful as a medicine for ulcer.

Another object of this invention is to provide processes for preparation of said imidazoisoquinoline compounds and pharmaceutically acceptable salts thereof A further object of this invention is to provide pharmaceutical composition comprising, as an active ingredient, said imidazoisoquinoline compound or its pharmaceutically acceptable salt.

Still further object of this invention is to provide method of using said imidazoisoquinoline compound or its pharmaceutically acceptable salt in the treatment of ulcer in human being and animals.

The imidazoisoquinoline compounds of this invention are novel and can be represented by the following general formula (I):

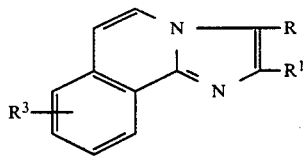
(I)

wherein
$R^1$ is lower alkyl,
$R^3$ is hydrogen, halogen or ar(lower)alkoxy, and
R is lower alkanoyl, nitroso, amino, carboxy, protected carboxy, carbamoyl, hydroxycarbamoyl, haloformyl, aminomethyleneamino which may be substituted with cyano or lower alkyl, iminomathylamino which may be substituted with cyano or lower alkyl, or a group of the formula: $-A-R^2$ in which
A is lower alkylene and
$R^2$ is di(lower)alkylamino, cyano, lower alkoxy, N-containing heterocyclic group which may have suitable substituent(s), lower alkynyloxy, lower alkenyloxy, lower alkylthio, amino(lower)alkythio, lower alkylsulfinyl, loweralkylsulfonyl, carboxyl, carbamoyl, hydroxycarbamoyl, hydroxy, lower alkanoyloxy, heterocyclicamino(lower)alkylthio having two oxo groups, hydrogen or a group of the formula:

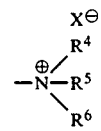

in which
$R^4$, $R^5$ and $R^6$ are each lower alkyl and X is an acid residue.

According to this invention, the object compounds (I) and their salts can be prepared by the following processes.

Process 1

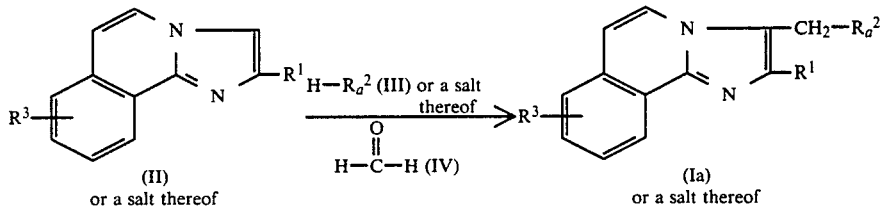

(II) or a salt thereof     (Ia) or a salt thereof

Process 2

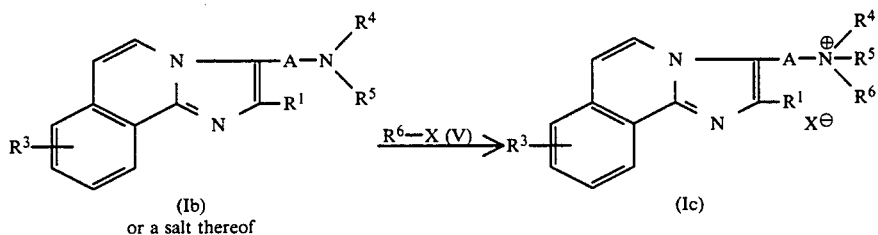

(Ib) or a salt thereof     (Ic)

Process 3

-continued
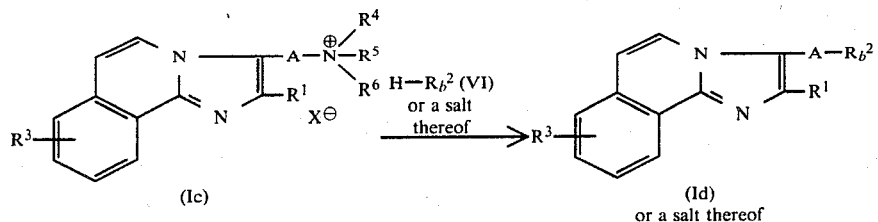
Process 4
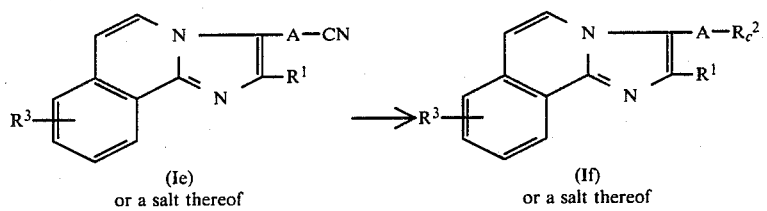
Process 5
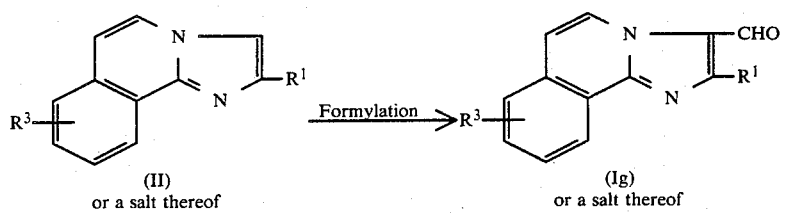
Process 6
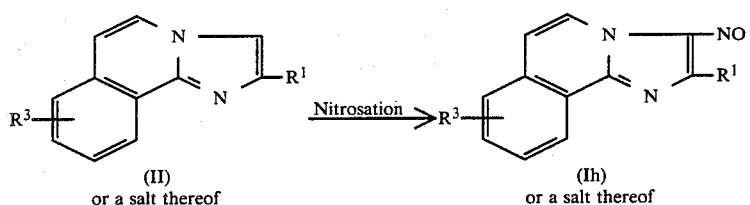
Process 7
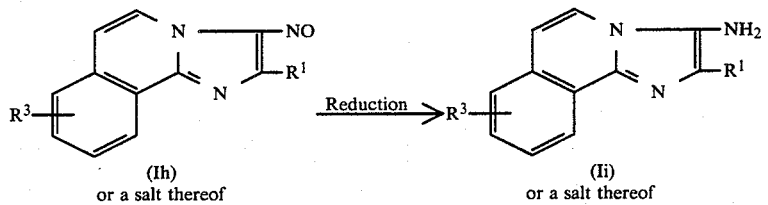
Process 8
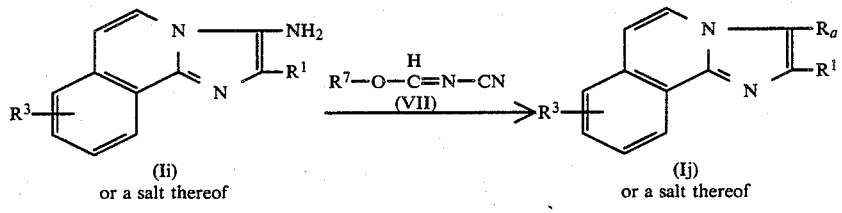
Process 9

-continued

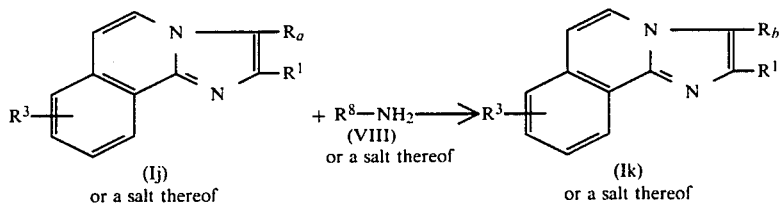

(Ij) or a salt thereof  +  R⁸—NH₂ (VIII) →  (Ik) or a salt thereof

Process 10

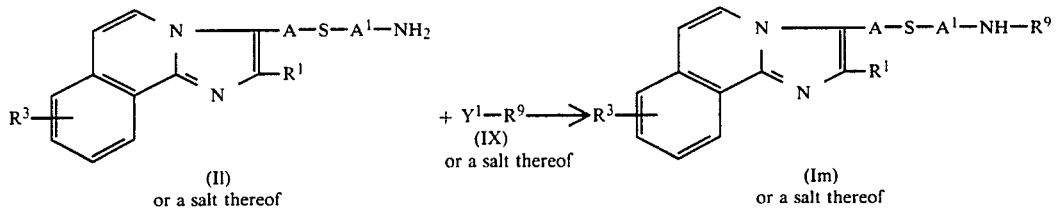

(Il) or a salt thereof  +  Y¹—R⁹ (IX) →  (Im) or a salt thereof

Process 11

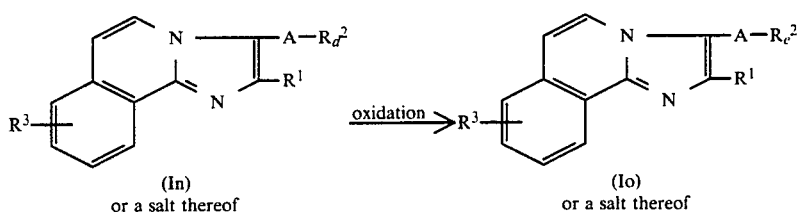

(In) or a salt thereof  —oxidation→  (Io) or a salt thereof

Process 12

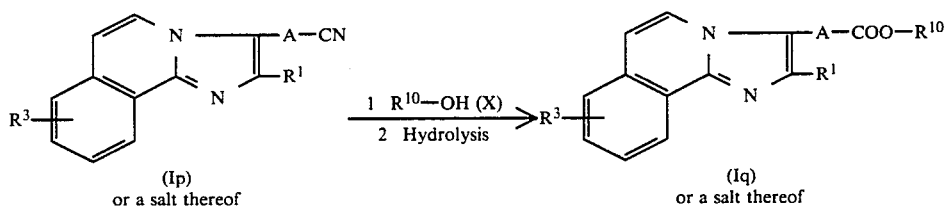

(Ip) or a salt thereof  $\xrightarrow{\text{1  R}^{10}\text{—OH (X)}}{\text{2  Hydrolysis}}$  (Iq) or a salt thereof Process 13

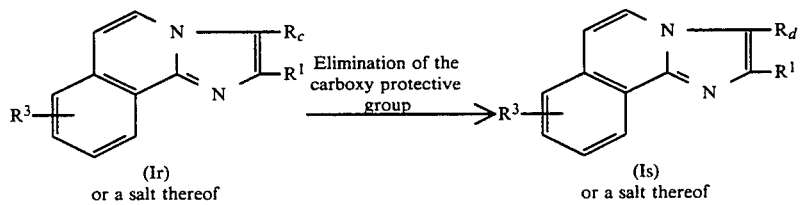

(Ir) or a salt thereof  —Elimination of the carboxy protective group→  (Is) or a salt thereof Process 14

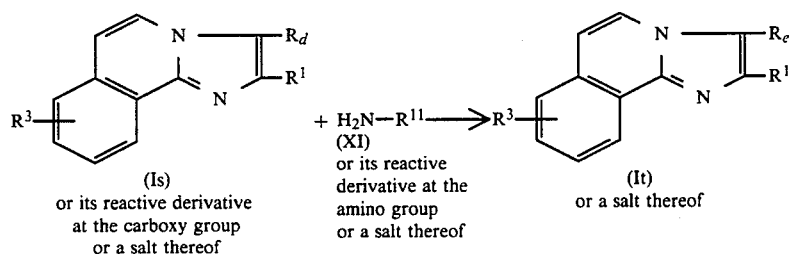

(Is) or its reactive derivative at the carboxy group or a salt thereof  +  H₂N—R¹¹ (XI) or its reactive derivative at the amino group or a salt thereof  →  (It) or a salt thereof Process 15

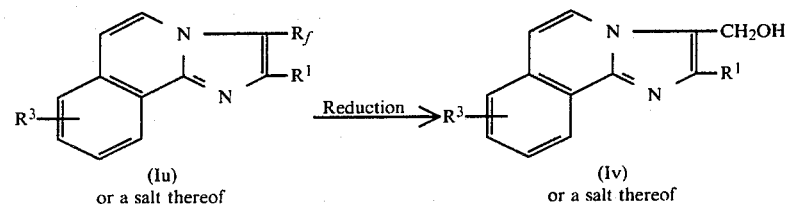

(Iu) or a salt thereof → Reduction → (Iv) or a salt thereof

Process 16

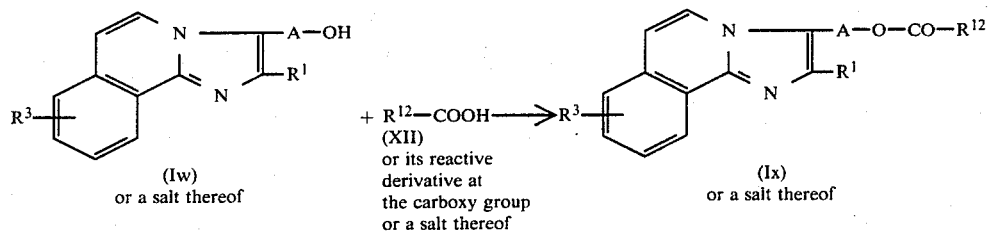

(Iw) or a salt thereof + R$^{12}$—COOH (XII) or its reactive derivative at the carboxy group or a salt thereof → (Ix) or a salt thereof Process 17

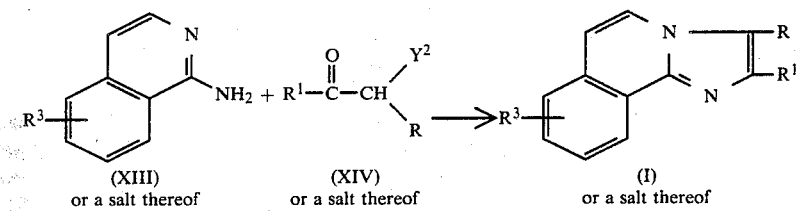

(XIII) or a salt thereof + (XIV) or a salt thereof → (I) or a salt thereof wherein R, R$^1$, R$^3$, R$^4$, R$^5$, R$^6$, A and X are each as defined above, R$_a^2$ is di(lower)alkylamino or N-containing heterocyclic group which may have suitable substituent(s), R$_b^2$ is cyano, lower alkoxy, di(lower)alkylamino, N-containing heterocyclic group which may have suitable substituent(s), lower alkynyloxy, lower alkenyloxy, lower alkylthio, amino(lower)alkylthio or heterocyclicamino(lower)alkylthio having two oxo groups, R$_c^2$ is tetrazol-5-yl, R$^7$ is lower alkyl, R$_a$ is cyanoaminomethyleneamino or cyanoiminomethylamino, R$^8$ is lower alkyl, R$_b$ is lower alkylaminomethyleneamino or lower alkyliminomethylamino, A$^1$ is lower alkylene, R$^9$ is heterocyclic group having two oxo groups, Y$^1$ is halogen, R$_d^2$ is lower alkylthio, R$_e^2$ is lower alkylsulfinyl or lower alkylsulfonyl, R$^{10}$ is lower alkyl R$_c$ is protected carboxy or protected carboxy(lower)alkyl, R$_d$ is carboxy or carboxy(lower)alkyl, R$^{11}$ is hydrogen or hydroxy, R$_e$ is carbamoyl, hydroxycarbamoyl, carbamoyl(lower)alkyl or hydroxycarbamoyl(lower)alkyl, R$_f$ is carboxy or esterified carboxy, R$^{12}$ is lower alkyl, and Y$^2$ is halogen.

Some of the starting compounds (II) are novel and can be prepared by the following Process.

Process A (XIIIa) or a salt thereof + R$^1$—CO—CH$_2$—Y$^3$ (XV) →

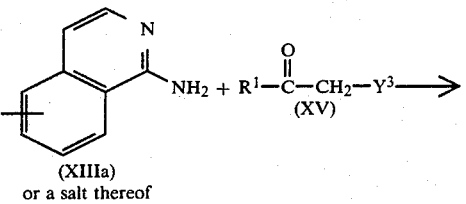

(IIa) or a salt thereof wherein

R$^1$ is as defined above,

R$_a^3$ is halogen or ar(lower)alkoxy, and

Y$^3$ is halogen.

Suitable pharmaceutically acceptable salts of the object compounds (I) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), a salt with an amino acid (e.g., arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "lower alkyl" and "lower alkyl moiety" in the terms "aminomethyleneamino which may be substituted with cyano or lower alkyl", "iminomethylamino which may be substituted with cyano or lower alkyl", "di(lower)alkylamino", "lower alkylthio", "amino(lower)alkylthio", "lower alkylsulfinyl", "lower alkylsulfonyl", "heteroyclicamino(lower)alkylthio having two oxo groups", "lower alkylaminomethyleneamino", "lower alkyliminomethylamino", "carboxy(lower)alkyl","protected carboxy(lower)alkyl", "carbamoyl(lower)alkyl" and "hydroxycarbamoyl(lower)alkyl" may include methyl, ethyl, propyl, isopropyl, butyl, t-butyl, pentyl, hexyl and the like.

Suitable "halogen" may include chlorine, bromine, fluorine, or iodine.

Suitable "ar(lower)alkoxy" may include phenyl(lower)alkoxy (e.g., benzyloxy, phenethyloxy, etc.) and the like.

Suitable "lower alkanoyl" and "lower alkanoyl moiety" in the term "lower alkanoyloxy" may include formyl, acetyl, propionyl, butyryl, isobutyryl, valeryl, isovaleryl, hexanoyl and the like.

Suitable "protected carboxy" and "protected carboxy moiety" in the term "protected carboxy(lower)alkyl" may include esterified carboxy and the like.

Suitable "ester moiety" in the term "esterified carboxy" may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)propionyloxyethyl ester, 1(or 2 or 3)-propionyloxypropyl ester, 1(or 2)-butyryloxyethyl ester, 1(or 2)isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.], lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), lower alkenyl ester (e.g. vinyl ester, allyl ester, etc.); lower alkynyl ester (e.g. etynyl ester, propynyl ester, etc.);

ar(lower)alkyl ester [e.g., mono(or di or tri)phenyl(lower)alkyl ester, etc.] which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.), and the like.

Suitable "haloformyl" may include fluoroformyl, chloroforml, bromoformyl and iodoformyl.

Suitable "lower alkylene" may include methylene, ethylene, trimethylene, tetramethylene, pentamethylene or hexamethylene.

Suitable "lower alkoxy" may include methoxy, ethoxy, propoxy, isopropoxy, butoxy, t-butoxy pentyloxy, hexyloxy and the like.

Suitable "N-containing heterocyclic group moiety" in the term "N-containing heterocyclic group which may have suitable substituent(s)" means saturated or unsaturated, monocyclic or polycyclic heterocyclic group containing nitrogen atom(s). And, especially preferable N-containing heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, triazolyl (e.g., 4H-1,2,4-triazolyl, 1H-1,2,3-triazolyl, 2H-1,2,3triazolyl, etc.), tetrazolyl (e.g., 1H-tetrazolyl, 2H-tetrazolyl, etc.), dihydrotriazinyl, etc.; saturated 3 to 8-membered heteromonocyclic group containing 1 to 4 nitrogen atom(s), for example, pyrrolidinyl, imidazolidinyl, piperidino, piperazinyl, etc.; unsaturated condensed heterocyclic group containing 1 to 5 nitrogen atom(s), for example, indolyl, isoindolyl, benzimidazolyl, 1H-indazolyl, etc.

Suitable substituent(s) in the term "N-containing heterocyclic group which may have suitable substituent(s)" may include lower alkyl (e.g., methyl, ethyl, propyl, isopropyl, butyl, isobutyl, t-butyl, pentyl, hexyl, etc.), hydroxy(lower)alkyl [e.g., hydroxymethyl, 1 or 2-hydroxyethyl, 1 or 2 or 3-hydroxypropyl, 1 or 2 or 3 or 4-hydroxybutyl, 1 or 2 or 3 or 4 or 5-hydroxypentyl, 1 or 2 or 3 or 4 or 5 or 6-hydroxyhexyl, etc.], and the like.

Suitable "lower alkynyloxy" may include ethynyloxy, propynyloxy, butynyloxy pentynyloxy, hexynyloxy and the like.

Suitable "lower alkenyloxy" may include vinyloxy, propenyloxy, butenyloxy, pentenyloxy, hexenyloxy and the like.

Suitable "heterocyclic moiety" in the terms "heterocyclicamino(lower)alkylthio having two oxo groups" and "heterocyclic group having two oxo groups" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6 membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 6-membered heteromonocyclic group containing 1 to 4 nitrogen atoms (e.g., pyrrolidinyl, imidazolidinyl, piperidino, piperazinyl, etc.); unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.;

unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5oxadiazolyl, etc.), etc.;

saturated 3 to 6-membered heteromonocyclic group containing 1 to 2 oxygen atoms and 1 to 3 nitrogen atoms (e.g., morpholinyl, etc.);

unsaturated condensed heterocyclic group containing 1 to 2 oxygen atoms and 1 to 3 nitrogen atoms (e.g., benzoxazolyl, benzoxadiazolyl, etc.);

unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.), etc.;

saturated 3 to 6-membered heteromonocyclic group containing 1 to 2 sulfur atoms and 1 to 3 nitrogen atoms (e.g., thiazolidinyl, etc.);

unsaturated condensed heterocyclic group containing 1 to 2 sulfur atoms and 1 to 3 nitrogen atoms (e.g., benzothiazolyl, 1,2-benzisothiazolyl, 2,1-benzisothiazolyl, benzothiadiazolyl, etc.) and the like.

Suitable "acid residue" may include a residue of an acid such as hydrohalogenic acid [i.e. halogen (e.g., chlorine, bromine, fluorine or iodine)], (lower)alkylsulfuric acid (e.g., methylsulfuric acid, ethylsulfuric acid, etc.) or the like.

Preferable embodiments of the object compounds (I) are as follows.

Preferable embodiment of $R^1$ is lower alkyl (more preferably methyl);

$R^3$ is hydrogen, halogen (more preferably chlorine) or ar(lower)alkoxy[more preferably phenyl(lower)alkoxy, most preferably benzyloxy]; and R is lower alkanoyl, nitroso, amino, carboxy, protected carboxy [more preferably esterified carboxy, most preferably lower alkoxycarbonyl], carbamoyl, hydroxycarbamoyl, haloformyl, cyanoaminomethyleneamino, lower alkylaminomethyleneamino, cyanoiminomethylamino, lower alkyliminomethylamino, or a group of the formula: —A—$R^2$ in which A is lower alkylene (more preferably methylene) and $R^2$ is di(lower)alkylamino (more preferably dimethylamino), cyano, lower alkoxy (more preferably methoxy or ethoxy), N-containing heterocyclic group which may have lower alkyl or hydroxy(lower)alkyl [more preferably saturated 3 to 8-membered heteromonocyclic group containing 1 to 4 nitrogen atom(s) which have hydroxy(lower)alkyl or unsaturated 3 to 8-membered heteromonocyclic group containing 1 to 4 nitrogen atom(s) which may have lower alkyl, most preferably piperazinyl having hydroxy(lower)alkyl, imidazolyl, tetrazolyl or imidazolyl having lower alkyl], lower alkynyloxy, lower alkenyloxy, lower alkylthio, amino(lower)alkylthio, lower alkylsulfinyl, lower alkylsulfonyl, carboxy, protected carboxy (more preferably esterified carboxy, most preferably lower alkoxycarbonyl), carbamoyl, hydroxycarbamoyl, hydroxy, lower alkanoyloxy, benzisothiazolylamino(lower)alkylthio having two oxo groups [more preferably (1,1-dioxo-1,2-benzisothiazolyl)amino(lower)alkylthio], hydrogen or a group of the formula:

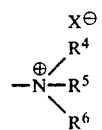

in which
$R^4$, $R^5$ and $R^6$ are each lower alkyl,
X is an acid residue (more preferably residue of lower alkylsulfuric acid, or halogen).

The processes for preparing the object compounds of the present invention are explained in detail in the following.

PROCESS 1

The compound (Ia) or a salt thereof can be prepared by reacting the compound (II) or a salt thereof with the compound (III) or a salt thereof and the compound (IV).

Suitable salts of the compounds (Ia) and (III) can be referred to the ones as exemplified for the compound (I).

Suitable salt of the compound (II) can be referred to the acid addition salt as exemplified for the compound (I).

The present reaction is usually carried out in the presence of a conventional acid. Suitable acid may include an organic acid (e.g. formic acid, acetic acid, propionic acid, trifluoroacetic acid, etc.) and an inorganic acid (e.g. hydrochloric acid, hydrobromic acid, sulfuric acid, etc.).

The reaction is usually carried out in a solvent such as water, methylene chloride, N,N-dimethylformamide, an alcohol (e.g. methanol, ethanol, etc.), a mixture thereof or any other solvent which does not adversely influence the reaction. A liquid acid can be also used as the solvent. The reaction temperature is not critical and the reaction is usually carried out under cooling to heating.

PROCESS 2

The compound (Ic) can be prepared by reacting the compound (Ib) or a salt thereof with the compound (V).

Suitable salt of the compound (Ib) can be referred to the acid addition salt as exemplified for the compound (I).

This reaction is usually carried out in a solvent such as alcohol (e.g. methanol, ethanol, etc.), benzene, N,N-dimethylformamide, tetrahydrofuran, acetone, diethyl ether or any other solvent which does not adversely affect the reaction.

In case that the compound (V) to be used is liquid, it can also be used as a solvent.

The reaction temperature is not critical and the reaction is usually carried out under cooling to warming.

PROCESS 3

The compound (Id) or a salt thereof can be prepared by reacting the compound (Ic) with the compound (VI) or a salt thereof.

Suitable salts of the compounds (Id) and (VI) can be referred to the ones as exemplified for the compound (I).

This reaction is usually carried out in a solvent such as alcohol [e.g. methanol, ethanol, etc.], dimethyl sulfoxide, benzene, N,N-dimethylformamide, tetrahydrofuran, diethyl ether of any other solvent which does not adversely affect the reaction.

In case that the compound (VI) or a salt thereof to be used in liquid, it can also be used as a solvent.

The reaction temperature is not critical and the reaction is usually carried out at ambient temperature, or under warming or heating.

PROCESS 4

The compound (If) or a salt thereof can be prepared by reacting the compound (Ie) or a salt thereof with an azide compound.

Suitable salts of the compounds (Ie) and (If) can be referred to the acid addition salt as exemplified for the compound (I).

Suitable example of the azide compound may be an inorganic base salt of azide [e.g. sodium azide, potassium azide, lithium azide, calcium azide, barium azide, etc.], hydrogen azide, hydrazonic acid, ammonium azide or the like.

This reaction is usually carried out in a solvent such as alcohol [e.g. methanol, ethanol, etc.], benzene, N,N-dimethylformamide, tetrahydrofuran, diethyl ether or any other solvent which does not adversely affect the reaction.

The reaction temperature is not critical and the reaction is usually carried out under warming or heating.

PROCESS 5

The compound (Ig) or a salt thereof can be prepared by subjecting the compound (II) or a salt thereof to formylation reaction.

Suitable salt of the compound (Ig) can be referred to the acid addition salt as exemplified for the compound (I).

This formylation can be carried out by a conventional method, for example by reacting the compound (II) or a salt thereof with Vilsmeier reagent (prepared by the reaction of N,N-dimethylformamide with phosphoryl chloride, etc.) (first step) and then subjecting the resultant compound to hydrolysis (second step).

(i) First step:

This reaction is usually carried out in a solvent such as alcohol [e.g. methanol, ethanol, etc.], benzene, N,N-dimethylformamide, tetrahydrofuran, diethyl ether or any other solvent which does not adversely affect the reaction.

The reaction temperature is not critical and the reaction is usually carried out under warming or heating.

(ii) Second step (hydrolysis):

Hydrolysis can be carried out by a conventional method.

PROCESS 6

The compound (Ih) or a salt thereof can be prepared by subjecting the compound (II) or a salt thereof to nitrosation reaction.

Suitable salt of the compound (Ih) can be referred to the acid addition salt as exemplified for the compound (I).

Suitable nitrosating agent to be used in this reaction may include lower alkyl nitrite (e.g., t-butyl nitrite, amyl nitrite, isoamyl nitrite, etc.) and the like.

This reaction is usually carried out in a solvent such as alcohol [e.g. methanol, ethanol, etc.], benzene, N,N-dimethylformamide, tetrahydrofuran, dioxane, diethyl ether or any other solvent which does not adversely affect the reaction.

The reaction temperature is not critical and the reaction is usually carried out under warming or heating.

PROCESS 7

The compound (Ii) or a salt thereof can be prepared by subjecting the compound (Ih) or a salt thereof to reduction reaction.

Suitable salt of the compound (Ii) can be referred to the acid addition salt as exemplified for the compound (I).

The reduction method applicable for this reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladium-carbon, etc.).

This reaction is usually carried out in a solvent such as water, alcohol [e.g. methanol, ethanol, etc.], benzene, N,N-dimethylformamide, tetrahydrofuran, diethyl ether or any other solvent which does not adversely affect the reaction.

The reaction temperature is not critical and the reaction is usually carried out under cooling to heating.

PROCESS 8

The compound (Ij) or a salt thereof can be prepared by reacting the compound (Ii) or a salt thereof with the compound (VII).

Suitable salt of the compound (Ij) can be referred to the acid addition salt as exemplified for the compound (I).

This reaction is usually carried out in a solvent such as alcohol [e.g. methanol, ethanol, etc.], benzene, N,N-dimethylformamide, tetrahydrofuran, diethyl ether or any other solvent which does not adversely affect the reaction.

The reaction temperature is not critical and the reaction is usually carried out under cooling to heating.

PROCESS 9

The compound (Ik) or a salt thereof can be prepared by reacting the compound (Ij) or a salt thereof with the compound (VIII) or a salt thereof.

Suitable salts of the compounds (Ik) and (VIII) can be referred to the acid addition salt as exemplified for the compound (I).

This reaction is usually carried out in a solvent such as water alcohol [e.g. methanol, ethanol, etc.], benzene, N,N-dimethylformamide, tetrahydrofuran, diethyl ether or any other solvent which does not adversely affect the reaction.

The reaction temperature is not critical and the reaction is usually carried out under cooling to heating.

PROCESS 10

The compound (Im) or a salt thereof can be prepared by reacting the compound (Il) or a salt thereof with the compound (IX) or a salt thereof.

Suitable salts of the compounds (Il), (Im) and (IX) can be referred to the acid addition salt as exemplified for the compound (I).

This reaction is usually carried out in the presence of base.

Suitable base may include an inorganic base such as alkali metal hydride (e.g. sodium hydride, etc.) alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine or the like.

This reaction is usually carried out in a solvent such as alcohol [e.g. methanol, ethanol, etc.], benzene, N,N-dimethylformamide, tetrahydrofuran, diethyl ether or any other solvent which does not adversely affect the reaction.

The reaction temperature is not critical and the reaction is usually carried out under cooling to heating.

PROCESS 11

The compound (Io) or a salt thereof can be prepared by subjecting the compound (In) or a salt thereof to oxidation reaction.

Suitable salts of the compounds (In) and (Io) can be referred to the acid addition salt as exemplified for the compound (I).

The present oxidation reaction can be carried out by a conventional method, for example by using an oxidizing agent such as m-chloroperbenzoic acid, perbenzoic acid, peracetic acid, ozone, hydrogen peroxide, periodic acid or the like.

This reaction is usually carried out in a solvent such as benzene, N,N-dimethylformamide, tetrahydrofuran, chloroform, diethyl ether or any other solvent which does not adversely affect the reaction.

The reaction temperature is not critical and the reaction is usually carried out under cooling or at ambient temperature.

PROCESS 12

The compound (Iq) or a salt thereof can be prepared by reacting the compound (Ip) or a salt thereof with the compound (X) (first step) and then subjecting the resultant compound to hydrolysis (second step).

Suitable salts of the compounds (Ip) and (Iq) can be referred to the acid addition salt as exemplified for the compound (I).

(i) First step:

This reaction is usually carried out in the presence of acid. Suitable acid may include an organic acid (e.g. formic acid, acetic acid, propionic acid, trifluoroacetic acid, etc.) and an inorganic acid (e.g. hydrochloric acid, hydrobromic acid, sulfuric acid, etc.).

This reaction is usually carried out in a solvent such as alcohol [e.g. methanol, ethanol, etc.], benzene, N,N-dimethylformamide, tetrahydrofuran, diethyl ether or any other solvent which does not adversely affect the reaction.

The reaction temperature is not critical and the reaction is usually carried out under warming or heating.

(ii) Second step (hydrolysis):

Hydrolysis can be carried out by a conventional method.

PROCESS 13

The compound (Is) or a salt thereof can be prepared by subjecting the compound (Ir) or a salt thereof to elimination reaction of the carboxy protective group.

Suitable salt of the compound (Is) can be referred to the ones as exemplified for the compound (I).

Suitable salt of the compound (Ir) can be referred to the acid addition salt as exemplified for the compound (I).

The present reaction is carried out in accordance with a conventional method such as hydrolysis, reduction or the like.

Hydrolysis is preferably carried out in the presence of a base or an acid. Suitable base may include an inorganic base and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), or the like. Suitable acid may include an organic acid (e.g. formic acid, acetic acid, propionic acid, trifluoroacetic acid, etc.) and an inorganic acid (e.g. hydrochloric acid, hydrobromic acid, sulfuric acid, etc.).

Reduction is carried out in a conventional manner, including chemical reduction and catalytic reduction.

The reaction is usually carried out in a solvent such as water, methylene chloride, an alcohol (e.g. methanol, ethanol, etc.), a mixture thereof or any other solvent which does not adversely influence the reaction. A liquid base or acid can be also used as the solvent. The reaction temperature is not critical and the reaction is usually carried out under cooling to heating.

PROCESS 14

The compound (It) or a salt thereof can be prepared by reacting the compound (Is) or its reactive derivative at the carboxy group or a salt thereof with the compound (XI) or its reactive derivative at the amino group or a salt thereof.

Suitable salts of the compounds (Is) and (It) can be referred to the ones as exemplified for the compound (I).

Suitable salt of the compound (XI) can be referred to the acid addition salt as exemplified for the compound (I).

Suitable reactive derivative at the carboxy group of the compound (Is) may include an acid halide, an acid anhydride, an activated amide, an activated ester and the like.

This reaction is usually carried out in a solvent such as water alcohol [e.g. methanol, ethanol, etc.], benzene, N,N-dimethylformamide, tetrahydrofuran, diethyl ether or any other solvent which does not adversely affect the reaction.

The reaction temperature is not critical and the reaction is usually carried out under cooling to warming.

PROCESS 15

The compound (Iv) or a salt thereof can be prepared by subjecting the compound (Iu) or a salt thereof to reduction reaction.

Suitable salts of the compounds (Iu) and (Iv) can be referred to the ones as exemplified for the compound (I).

Suitable reducing agent may include lithium aluminum hydride and the like.

This reaction is usually carried out in a solvent such as alcohol [e.g. methanol, ethanol, etc.], benzene, N,N-dimethylformamide, tetrahydrofuran, diethyl ether or any other solvent which does not adversely affect the reaction.

The reaction temperature is not critical and the reaction is usually carried out under cooling or at ambient temperature.

PROCESS 16

The compound (Ix) or a salt thereof can be prepared by reacting the compound (Iw) or a salt thereof with the compound (XII) or its reactive derivative at the carboxy group or a salt thereof.

Suitable salt of the compound (Iw) can be referred to the ones as exemplified for the compound (I).

Suitable salt of the compound (XII) may include an alkali metal salt (e.g., sodium salt, potassium salt, etc.) and the like.

Suitable salt of the compound (Ix) can be referred to the acid addition salt as exemplified for the compound (I).

Suitable reactive derivative at the carboxy group of the compound (XII) can be referred to the ones as exemplified for the compound (Is).

This reaction is usually carried out in a solvent such as benzene, N,N-dimethylformamide, tetrahydrofuran, pyridine, diethyl ether or any other solvent which does not adversely affect the reaction.

The reaction temperature is not critical and the reaction is usually carried out under cooling to warming.

PROCESS 17

The compound (I) or a salt thereof can be prepared by reacting the compound (XIII) or a salt thereof with the compound (XIV) or a salt thereof.

Suitable salt of the compound (XIV) can be referred to the ones as exemplified for the compound (I).

Suitable salt of the compound (XIII) can be referred to the acid addition salt as exemplified for the compound (I).

This reaction is usually carried out in a solvent such as alcohol [e.g. methanol, ethanol, etc.], benzene, chloroform, N,N-dimethylformamide, tetrahydrofuran, diethyl ether or any other solvent which does not adversely affect the reaction.

The reaction may be preferably carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], tri(lower)alkylamine [e.g. trimethylamine, triethylamine, etc.], pyridine or its derivative [e.g. picoline, lutidine, 4-dimethylaminopyridine, etc.], or the like. In case that the base to be used is liquid, it can also be used as a solvent.

The reaction temperature is not critical, and the reaction can be carried out under cooling, at ambient temperature or under warming or heating.

The process for preparing the starting compound (IIa) is explained in detail in the following.

PROCESS A

The compound (IIa) or a salt thereof can be prepared by reacting the compound (XIIIa) or a salt thereof with the compound (XV).

Suitable salts of the compounds (IIa) and (XIIIa) can be referred to the acid addition salt as exemplified for the compound (I). The present reaction can be carried out in a similar manner to that of aforementioned Process 17.

The object compounds (I) and their pharmaceutically acceptable salts of the present invention are novel and exhibit high inhibitory activity on ulcer.

In order to illustrate the usefulness of the object compound (I), the pharmacological data of some of the object compounds (I) are shown in the following.

(A) Inhibition on ethanol ulcer

Test Method:

Five male Sprague-Dawley rates, aged 7 weeks and weighing about 200 g, were used per group for the study on ethanol ulcer after the fast for 24 hours.

Test compound was suspended in 0.1% methylcellulose aqueous solution, and the suspension (5 ml/kg) was orally given to each rat.

The control group was given a vehicle, i.e. 0.1% methylcellulose aqueous solution (5 ml/kg), alone in the same way.

Absolute ethanol (5 ml/kg) was orally administered 30 minutes after dosing with test compound, and one hour later, the rats were sacrificed and their stomachs were removed. The area of ulcers of each rat was measured. The mean area ($mm^2$) in the medicated group was compared with that in the control group.

Test Result:

Test Compound: 7-Chloro-3-cyanomethyl-2-methyl imidazo[2,1-a]isoquinoline

The $ED_{50}$ value of the test compound: 0.97 mg/kg (B) Inhibition on stress ulcer Test Method:

Five Sprague-Dawley rats weighing about 200 g were used per group. Each animal was immobilized in a small cage and put in a water bath allowing to respire. The temperature of the water bath kept at 22° C. The test compound was administered orally just before the immobilization. Seven hours later, the animals were sacrificed and their stomachs were removed. The stomach was then fixed with 2% formalin. The area of ulcers was measured for each animal. The mean area ($mm^2$) in the medicated animals was compared with that in the control animals.

Test Result:

Test Compound: 7-Chloro-3-cyanomethyl-2-methylimidazo[2,1-a]isoquinoline

The $ED_{50}$ value of the test compound: 1.8 mg/kg

As being apparent from the above test results, the object compound (I) of the present invention are useful as antiulcer medicines.

For therapeutic purpose, the compounds according to the present invention can be used in a form of pharmaceutical preparation containing said compound as an active ingredient, in admixture with a pharmaceutically acceptable carrier such as an organic or inorganic solid or liquid excipient suitable for oral or parenteral administration. The pharmaceutical preparations may be capsules, tablets, dragees, solution, suspension, emulsion, and the like. If desired, there may be included in the above preparations auxiliary substances, stabilizing agents, wetting or emulsifying agents, buffers and other commonly used additives.

While the dosage of the compounds will vary depending upon the age and condition of the patient, an average single dose of about 5 mg, 10 mg, 50 mg, 100 mg, 250 mg, 500 mg, and 1000 mg of the compounds according to the present invention may be effective for treating ulcer. In general, amounts between 1 mg/body and about 6,000 mg/body or even more may be administered per day.

The following preparations and examples are given for the purpose of illustrating the present invention.

PREPARATION 1

A mixture of 5-chloro-1-aminoisoquinoline (2.8 g), chloroacetone (5.4 g) and sodium bicarbonate (7.6 g) in anhydrous ethanol (35 ml) was heated at 60° C. for 16 hours and filtered by suction. The filtrate was evaporated in vacuo and the residual solid was washed with ethanol to give 7-chloro-2-methylimidazo[2,1-a]isoquinoline (2.8 g).

mp: 188° to 191° C.

IR (Nujol): 1470, 1390, 800 cm$^{-1}$

NMR (CDCl$_3$, δ): 2.47 (3H, s), 7.22–7.84 (5H, m), 8.40–8.53 (1H, m)

PREPARATION 2

The following compounds were obtained according to a similar manner to that of Preparation 1.

(1) 7-Benzyloxy-2-methylimidazo[2,1-a]isoquinoline mp: 89° to 90° C.

IR (Nujol): 1602, 1550, 1510, 1482, 1260 cm$^{-1}$

NMR (CDCl$_3$, δ): 2.50 (3H, s), 5.17 (2H, s), 6.93 (1H, d, J=8 Hz), 7.10–7.80 (9H, m), 8.14 (1H, d, J=8 Hz)

(2) 8-Chloro-2-methylimidazo[2,1-a]isoquinoline mp: 131° to 133° C.

IR (Nujol): 1625, 1510 cm$^{-1}$

NMR (DMSO-d$_6$, δ): 2.38 (3H, s), 7.12 (1H, d, J=7.5 Hz), 7.58 (1H, dd, J=9.5 Hz, 2 Hz), 7.68 (1H, s), 7.92 (1H, d, J=2 Hz), 8.28 (1H, d, J=7.5 Hz), 8.37 (1H, d, J=9.5 Hz)

EXAMPLE 1

To a solution of 37% aqueous formaldehyde (0.42 g) and 50% aqueous dimethylamine (0.46 g) in acetic acid (3.2 ml) was added 7-chloro-2-methylimidazo[2,1-a]isoquinoline (1 g) and the mixture was warmed at 50° C. with stirring for 3.5 hours. The solution was poured into ice water and neutralized with an aqueous solution of sodium hydroxide. The resulting precipitates were collected by filtration, washed with water and recrystallized from a mixture of toluene and n-hexane to give 7-chloro-3-dimethylaminomethyl-2-methylimidazo[2,1-a]isoquinoline (0.9 g).

mp: 157° to 160° C.

IR (Nujol): 1520, 1480, 1400, 1380, 1370, 1020, 780 cm$^{-1}$

NMR (CDCl$_3$, δ): 2.20 (6H, s), 2.47 (3H, s), 3.63 (2H, s), 7.24–8.60 (5H, m)

Analysis Calcd. for C$_{15}$H$_{16}$ClN$_3$: C 65.81, H 5.89, N 15.35, Cl 12.95. Found: C 65.86, H 5.80, N 15.16, Cl 12.59.

EXAMPLE 2

The following compounds were obtained according to a similar manner to that of Example 1.

(1) 3-Dimethylaminomethyl-2-methylimidazo[2,1-a]isoquinoline mp: 97° to 99° C.

IR (Nujol): 1710, 1450, 1390, 1380, 1370 cm$^{-1}$

NMR (CDCl$_3$, δ): 2.24 (6H, s), 2.48 (3H, s), 3.65 (2H, s), 7.00 (1H, d, J=8 Hz), 7.47–7.77 (3H, m), 8.06 (1H, d, J=8 Hz), 8.64–8.73 (1H, m)

Analysis Calcd. for C$_{15}$H$_{17}$N$_3$: C 75.28, H 7.16, N 17.56. Found: C 74.97, H 7.11, N 17.35.

(2) 7-Benzyloxy-3-dimethylaminomethyl-2-methylimidazo[2,1-a]isoquinoline mp: 135° to 137° C.

IR (Nujol): 1600, 1560, 1510, 1480, 1263 cm$^{-1}$

NMR (CDCl$_3$, δ): 2.23 (6H, s), 2.50 (3H, s), 3.67 (2H, s), 5.28 (2H, s), 6.97–7.70 (8H, m), 8.00–8.40 (2H, m)

(3) 8-Chloro-3-dimethylaminomethyl-2-methylimidazo[2,1-a]isoquinoline mp: 117° to 120° C.

IR (Nujol): 1635, 1515 cm$^{-1}$

NMR (DMSO-d$_6$, δ): 2.18 (6H, s), 2.38 (3H, s), 3.70 (2H, s), 7.17 (1H, d, J=7.5 Hz), 7.60 (1H, dd, J=9 Hz, 2 Hz), 7.95 (1H, d, J=2 Hz), 8.22 (1H, d, J=7.5 Hz), 8.38 (1H, d, J=9 Hz)

EXAMPLE 3

To a solution of 37% aqueous formaldehyde (1.5 g), 1-(2-hydroxyethyl)piperazine (2.35 g), water (2 ml) and acetic acid (12 ml) was added 2-methylimidazo [2,1-a]isoquinoline (3 g) and the solution was warmed at 50° C. with stirring for 3 hours. The solution was poured into ice water and neutralized with an aqueous solution of sodium hydroxide.

The resulting precipitates were collected by filtration, washed with water and chromatographed on silica gel (60 g) with a mixture of chloroform and methanol (10:1) as an eluent. The eluates were evaporated in vacuo and the residual solid was recrystallized from a mixture of ethyl acetate and n-hexane to give 3-[4-(2-hydroxyethyl)-1-piperazinylmethyl]-2-methylimidazo[2,1-a]isoquinoline (2.2 g).

mp: 115° to 117° C.

IR (Nujol): 3200, 2800, 1515, 1410, 1340, 1160, 1080, 1010 cm$^{-1}$

NMR (CDCl$_3$, δ): 2.33–2.60 (13H, m), 3.63 (2H, s), 3.70 (2H, s), 7.00 (1H, d, J=8 Hz), 7.33–7.78 (3H, m), 8.03 (1H, d, J=8 Hz), 8.50–8.70 (1H, m)

Analysis Calcd. for C$_{19}$H$_{24}$N$_4$O: C 70.34, H 7.46, N 17.27. Found: C 70.77, H 7.54, N 17.18.

EXAMPLE 4

A solution of 7-chloro-3-dimethylaminomethyl-2-methylimidazo[2,1-a]isoquinoline (3.4 g) in tetrahydrofuran (30 ml) was added dropwise to a solution of dimethyl sulfate (3.5 ml) in tetrahydrofuran (20 ml) with ice-cooling and stirring. After being stirred for 2 hours under the same conditions, the resulting precipitates were collected by filtration and washed with tetrahydrofuran and then ethanol to give 7-chloro-2-methyl-3-trimethylammoniomethylimLdazo[2,1-a]isoquinoline methylsulfate (4.4 g).

mp: 220° to 223° C. (dec.)

IR (Nujol): 1390, 1360, 1230, 1050, 750 cm$^{-1}$

EXAMPLE 5

A solution of 3-dimethylaminomethyl-2-methylimidazo[2,1-a]isoquinoline (7.7 g) in tetrahydrofuran (20 ml) was added dropwise to a solution of dimethyl sulfate (15 ml) in tetrahydrofuran (40 ml) with ice-cooling and stirring, and the mixture was stirred for 2 hours under the same conditions. To the reaction mixture was added diethyl ether (60 ml) and stirred with ice-cooling for 1 hour. The resulting precipitates were collected by filtration, washed with diethyl ether and recrystallized from ethanol to give 2-methyl-3-trimethylammoniomethylimidazo[2,1-a]isoquinoline methylsulfate (10 g).

mp: 146° to 149° C.
IR (Nujol): 1630, 1550, 1510, 1240, 1220, 1010, 750 cm$^{-1}$

EXAMPLE 6

Methyliodide (1.7 g) was added dropwise to a solution of 8-chloro-3-dimethylaminomethyl-2-methylimidazo[2,1-a]isoquinoline (2.8 g) in ethanol (34 ml) at room temperature and the mixture was stirred for 14 hours. The resulting precipitate was collected by filtration, washed with ethanol and dried in a desiccator to give 8-chloro-2-methyl-3-trimethylammoniomethylimidazo[2,1-a]isoquinoline iodide (3.58 g).

mp: 169° to 170° C. (dec.)
IR (Nujol): 1630 cm$^{-1}$
NMR (DMSO-$d_6$, δ): 2.57 (3H, s), 3.15 (9H, s), 5.03 (2H, s), 7.40 (1H, d, J=7.5 Hz), 7.70 (1H, dd, J=9 Hz, 2 Hz), 8.05 (1H, d, J=2 Hz), 8.48 (1H, d, J=9 Hz), 8.67 (1H, d, J=7.5 Hz)

EXAMPLE 7

The following compound was obtained according to a similar manner to that of Example 6.

7-Benzyloxy-2-methyl-3-trimethylammoniomethylimidazo[2,1-a]isoquinoline iodide mp: 193° to 195° C. (dec.)
IR (Nujol): 1600, 1560, 1510, 1270 cm−1
NMR (DMSO-$d_6$, δ): 2.57 (3H, s), 3.20 (9H, s), 5.1 (2H, s), 5.33 (2H, s), 7.13-7.77 (8H, m), 8.06 (1H, d, J=8 Hz), 8.63 (1H, d, J=8 Hz)

EXAMPLE 8

A mixture of 7-chloro-2-methyl-3-trimethylammoniomethylimidazo[2,1-a]isoquinoline methylsulfate (2 g), sodium cyanide (0.32 g) in dimethyl sulfoxide (10 ml) was heated at 100° C. with stirring for 3 hours and cooled to room temperature. The mixture was poured into water and extracted with chloroform. The extract was washed with brine, dried over magnesium sulfate and evaporated in vacuo. The residue was chromatographed on silica gel (20 g) with a mixture of chloroform and methanol (10:1) as an eluent.

The eluates were evaporated in vacuo and the residual solid was recrystallized from ethanol to give 7-chloro-3-cyanomethyl-2-methylimidazo[2,1-a]isoquinoline (0.5 g).

mp: 199° to 203° C.
IR (Nujol): 2250, 1510, 1480, 1410, 1370 cm$^{-1}$
NMR (DMSO-$d_6$, δ): 2.45 (3H, s), 4.51 (2H, s), 7.37-7.85 (3H, m), 8.32-8.49 (2H, m)
Analysis Calcd. for $C_{14}H_{10}ClN_3$: C 65.75, H 3.94, N 16.43 Found: C 66.12, H 4.27, N 16.55.

EXAMPLE 9

The following compound was obtained according to a similar manner to that of Example 8.

3-Cyanomethyl-2-methylimidazo[2,1-a]isoquinoline mp: 167° to 170° C.
IR (Nujol): 2250, 1390, 790, 710 cm$^{-1}$
NMR (CDCl$_3$, δ): 2.43 (3H, s), 3.93 (2H, s), 7.03-7.80 (5H, m), 8.52-8.77 (1H, m)
Analysis Calcd. for $C_{14}H_{11}N_3$: C 75.99, H 5.01, N 18.99 Found: C 76.17, H 5.06, N 19.07.

EXAMPLE 10

A mixture of 2-methyl-3-trimethylammoniomethylimidazo[2,1-a]isoquinoline methylsulfate (4.5 g) and imidazole (2.02 g) in ethanol (45 ml) was refluxed with stirring for 7 hours and evaporated in vacuo. To the residue was added water and the resulting precipitates were collected by filtration and recrystallized from a mixture of ethyl acetate and n-hexane to give 3-(1-imidazolylmethyl)-2methylimidazo[2,1-a]isoquinoline (2.3 g).

mp: 189° to 191° C.
IR (Nujol): 1640, 1610, 1570, 1550, 1510 cm$^{-1}$
NMR (CDCl$_3$, δ): 2.53 (3H, s), 5.36 (2H, s), 6.60-7.20 (3H, m), 7.23-7.80 (5H, m), 8.50-8.80 (1H, m)
Analysis Calcd. for $C_{16}H_{14}N_4$: C 73.26, H 5.38, N 21.36 Found: C 72.77, H 5.37, N 21.00.

EXAMPLE 11

A mixture of 2-methyl-3-trimethylammoniomethylimidazo[2,1-a]isoquinoline methylsulfate (3 g) and 2-methylimidazole (1.6 g) in ethanol (50 ml) was refluxed with stirring for 4 hours and evaporated in vacuo. To the residue was added water and the resulting precipitates were collected by filtration, dried and recrystallized from ethyl acetate to give 2-methyl-3-(2-methyl-1-imidazolylmethyl)imidazo[2,1-a]isoquinoline (0.85 g).

mp: 182° to 184° C.
IR (Nujol): 3350, 3100, 1450, 1380, 1280 cm$^{-1}$
NMR (CDCl$_3$, δ): 2.43 (3H, s), 2.50 (3H, s), 5.20 (2H, s), 6.58-7.83 (7H, m), 8.59-8.82 (1H, m)
Analysis Calcd. for $C_{17}H_{16}N_4 \cdot \frac{1}{2}H_2O$: C 71.56, H 6.00, N 19.64, $H_2O$ 3.15. Found: C 71.43, H 5.91, N 19.37, $H_2O$ 3.30.

EXAMPLE 12

To a solution of 60% sodium hydride (0.235 g) in propargyl alcohol (9.36 ml) was added 7-chloro-2-methyl-3-trimethylammoniomethylimLdazo[2,1-a]isoquinoline iodide (2.08 g) and the mixture was heated at 100° C. with stirring for 2 hours. After being cooled, the mixture was evaporated in vacuo and the residue was dissolved in chloroform. The solution was washed with water, dried over magnesium sulfate and evaporated in vacuo. The residue was purified by column chromatography on silica gel (20 g) with a mixture of chloroform and methanol (100:1) as an eluent to give 7-chloro-2-methyl-3-propargyloxymethylimidazo[2,1-a]isoquinoline. This compound was treated with a solution of hydrogen chloride in ethanol to give 7-chloro-2-methyl-3-propargyloxymethylimidazo[2,1-a]isoquinoline hydrochloride (1 g).

mp: 210° to 216° C. (dec.)
IR (Nujol): 3200, 2360, 1645, 1580 cm$^{-1}$

NMR (CF$_3$COOH, δ): 2.70 (1H, t, J=2 Hz), 2.80 (3H, s), 4.47 (2H, d, J=2 Hz), 5.30 (2H, s), 7.73–8.73 (5H, m)

EXAMPLE 13

The following compounds were obtained according to similar manners to those of Examples 8 and 10 to 12.

(1)
7-Benzyloxy-3-cyanomethyl-2-methylimidazo[2,1-a]isoquinoline mp: 189° to 191° C.
IR (Nujol): 2250, 1600, 1570, 1550, 1260, 1010 cm$^{-1}$
NMR (CDCl$_3$, δ): 2.43 (3H, s), 3.83 (2H, s), 5.15 (2H, s), 7.00 (1H, d, J=8 Hz), 7.20–7.77 (8H, m), 8.17 (1H, d, J=8 Hz)

(2)
8-Chloro-3-cyanomethyl-2-methylimidazo[2,1-a]isoquinoline mp: 252° to 253° C. (dec.)
IR (Nujol): 2250, 1630 cm$^{-1}$
NMR (DMSO-d$_6$, δ): 2.42 (3H, s), 4.47 (2H, s), 7.33 (1H, d, J=7 Hz), 7.67 (1H, dd, J=9 Hz, 2 Hz), 8.03 (1H, d, J=2 Hz), 8.27 (1H, d, J=7Hz), 8.42 (1H, d, J=9 Hz)

(3)
7-Chloro-3-methoxymethyl-2-methylimidazo[2,1-a]isoquinoline mp: 148° to 149° C.
NMR (CDCl$_3$, δ): 2.53 (3H, s), 3.33 (3H, s), 4.75 (2H, s), 7.25–7.73 (3H, s), 8.02 (1H, d, J=7.5 Hz), 8.57 (1H, dd, J=7.5 Hz, 2.5 Hz)

(4)
3-Allyloxymethyl-7-chloro-2-methylimidazo[2,1-a]isoquinoline hydrochloride mp: 173° to 175° C. (dec.)
IR (Nujol): 2360, 1650, 1585, 1522 cm$^{-1}$
NMR (D$_2$O, δ): 2.64 (3H, s), 4.28 (2H, d, J=6 Hz), 4.90 (2H, s), 5.36 (1H, m), 5.60 (1H, m), 5.73–6.5 (1H, m), 7.30 (1H, d, J=8 Hz), 7.15–7.70 (3H, m), 8.0 (1H, d, J=8 Hz)

(5)
7-Chloro-2-methyl-3-methylthiomethylimidazo[2,1-a]isoquinoline mp: 146° to 148° C.
IR (Nujol): 1560, 1500, 1360 cm$^{-1}$
NMR (CF$_3$COOH, δ): 2.19 (3H, s), 2.69 (3H, s), 4.22 (2H, s), 7.87–8.72 (5H, m)

(6)
3-(2-Aminoethyl)thiomethyl-7-chloro-2-methylimidazo[2,1-a]isoquinoline mp: 94° C.
IR (Nujol): 3310, 1615, 1595, 1570, 1510 cm$^{-1}$
NMR (CDCl$_3$, δ): 1.83 (2H, s), 2.47 (3H, s), 2.20–2.97 (4H, m), 3.98 (2H, s), 7.20–7.70 (3H, m), 7.93 (1H, d, J=8 Hz), 8.50 (1H, dd, J=2 Hz, 7 Hz)

EXAMPLE 14

Ethanol (50 ml) was added to a mixture of 7-chloro-2-methyl-3-trimethylammoniomethylimidazo[2,1-a]isoquinoline methylsulfate (2.3 g) and imidazole (0.95 g) in dimethyl sulfoxide (20 ml) and heated at 100° C. with stirring for 5 hours. After the removal of ethanol by distillation, the residue was poured into water. The resulting precipitates were collected by filtration, dried and recrystallized from ethyl acetate. The obtained crystals were chromatographed on silica gel (16 g) with a mixture of chloroform and methanol (10:1) as an eluent. The eluates were evaporated in vacuo and the residual solid was recrystallized from ethyl acetate to give 7-chloro-3-(1-imidazolylmethyl)-2-methylimidazo[2,1-a]isoquinoline (0.7 g).

mp: 229° to 230° C.
IR (Nujol): 1390, 1370, 1220, 1080, 790 cm$^{-1}$
NMR (CDCl$_3$, δ): 2.58 (3H, s), 5.42 (2H, s), 6.84–7.70 (7H, m), 8.48–8.63 (1H, m)
Analysis Calcd. for C$_{16}$H$_{13}$ClN$_4$: C 64.76, H 4.41, N 18.88. Found: C 64.95, H 4.58, N 19.02.

The mother liquid was evaporated in vacuo and the residual solid was recrystallized from diethyl ether to give 7-chloro-3-ethoxymethyl-2methylimidazo[2,1-a]isoquinoline (0.2 g).

mp: 94° to 96° C.
IR (Nujol): 1380, 1360, 1180, 780 cm$^{-1}$
NMR (CDCl$_3$, δ): 1.21 (3H, t, J=7 Hz), 2.50 (3H, s), 3.53 (2H, q, J=7 Hz), 4.77 (2H, s), 7.23–8.61 (5H, m)
Analysis Calcd. for C$_{15}$H$_{15}$ClN$_2$O: C 65.57, H 5.50, N 10.20, Cl 12.91. Found: C 65.66, H 5.42, N 10.37, Cl 13.21.

EXAMPLE 15

A mixture of 3-cyanomethyl-2-methylimidazo[2,1-a]isoquinoline (2.8 g), ammonium chloride (0.74 g) and sodium azide (0.9 g) in N,N-dimethylformamide (28 ml) was heated at 120°–125° C. with stirring for 18 hours. The solution was poured into water, acidified with concentrated hydrochloric acid and then neutralized with an aqueous solution of sodium bicarbonate. The resulting precipitates were collected by filtration, washed with water and recrystallized from a mixture of chloroform and methanol to give 2-methyl-3-[(1H-tetrazol-5-yl)methyl]imidazo[2,1-a]isoquinoline (2.9 g).

mp: 256° to 257° C.
IR (Nujol): 3450, 2500 (broad), 1660, 1540 cm$^{-1}$
NMR (DMSO-d$_6$, δ): 2.12 (3H, s), 4.74 (2H, s), 6.70 (3H, br s), 7.18–8.55 (6H, m)
Analysis Calcd. for C$_{14}$H$_{12}$N$_6$.H$_2$O: C 59.56, H 4.99, N 29.77. Found: C 59.31, H 5.03, N 29.33.

EXAMPLE 16

A solution of 7-chloro-2-methylimidazo[2,1-a]isoquinoline (4 g) in N,N-dimethylformamide (40 ml) was added dropwise to a mixture of N,N-dimethylformamide (5.7 ml) and phosphoryl chloride (1.86 ml) under ice cooling. After being stirred at 85°–90° C. for 6 hours, the mixture was poured into ice-water, basified with aqueous sodium hydroxide, heated at 80° C. for 20 minutes and cooled. The resulting precipitate was collected by filtration, washed with water and recrystallized from methanol to give 7-chloro-3-formyl-2methylimidazo[2,1-a]isoquinoline (0.356 g).

mp: 213° to 214° C.
IR (Nujol): 1655 cm$^{-1}$
NMR (CF$_3$COOH, δ) : 3.13 (3H, s), 8.10–8.87 (4H, m), 9.72 (1H, d, J=7.5 Hz), 10.45 (1H, s)

EXAMPLE 17

Isoamyl nitrite (140 g) was added to a suspension of 7-chloro-2-methylimidazo[2,1-a]isoquinoline (17.1 g) in dioxane (170 ml) at 50° C. and the mixture was refluxed for 15 minutes. After being cooled, the resulting precipitate was collected by filtration, washed successively with dioxane and diethyl ether and dried in a desiccator to give 7-chloro-2-methyl-3-nitrosoimidazo[2,1-a]isoquinoline (7.7 g).

mp: >190° C. (dec.)

IR (Nujol): 1620, 1585, 1350, 1250, 1200 cm$^{-1}$

EXAMPLE 18

Zinc powder (10.2 g) was added portionwise to a mixture of 7-chloro-2-methyl-3-nitrosoimidazo[2,1-a]isoquinoline (7.7 g) and acetic acid (100 ml) in water (77 ml) over a period of 7 hours and then the mixture was filtered by suction. The filtrate was evaporated in vacuo and the residue was extracted with chloroform after an addition of aqueous sodium bicarbonte to it. The extract was washed with water and evaporated in vacuo. The residual solid was washed with ethyl acetate and dried in a desiccator to give 3-amino-7-chloro-2-methylimidazo[2,1-a]isoquinoline (5.85 g).

IR (Nujol): 3250, 3150, 1610, 1590, 1500 cm$^{-1}$

NMR (DMSO-d$_6$, δ): 2.33 (3H, s), 4.83 (2H, broad s), 7.28 (1H, d, J=8 Hz), 7.43–7.70 (2H, m), 8.10 (1H, d, J=8 Hz), 8.30 (1H, dd, J=4 Hz, 7 Hz)

EXAMPLE 19

Ethyl N-cyanoformimidate (3.2 g) was added to a suspension of 3-amino-7-chloro-2-methylimidazo[2,1-a]isoquinoline (2.3 g) in ethanol (60 ml) and the mixture was stirred at room temperature for 45 hours. The mixture was evaporated in vacuo and the residual solid was washed successively with diethyl ether and ethyl acetate to give N-cyano-N'-(7-chloro-2-methylimidazo[2,1-a]isoquinolin-3-yl)formamidine (1.0 g).

mp: 203° to 206° C. (dec.)

IR (Nujol): 3240, 2200, 1620, 1595 cm$^{-1}$

NMR (DMSO-d$_6$, δ): 2.33 (3H, s), 7.3–8.9 (6H, m)

EXAMPLE 20

Isopropylamine (2 ml) was added to a suspension of N-cyano-N'-(7-chloro-2-methylimidazo[2,1-a]isoquinolin-3-yl)formamidine (0.95 g) in water (1.5 ml) and the mixture was stirred at room temperature for 30 minutes. The resulting precipitate was collected by filtration, washed with water and dissolved in ethanol. To the solution was added a saturated solution of hydrogen chloride in ethanol and the mixture was evaporated in vacuo. The residual solid was washed successively with a mixture of diethyl ether and ethanol and isopropanol and then dried in a desiccator to give N-isopropyl-N'-(7-chloro-2-methylimldazo[2,1-a]isoquinolin-3-yl)formamidine dihydrochloride (0.73 g).

mp: 189° to 190° C.

NMR (DMSO-d$_6$, δ): 1.23 (3H, d, J=7 Hz), 1.34 (3H, d, J=7 Hz), 2.5 (3H, s), 4.0 (1H, m), 7.5–9.1 (6H, m)

EXAMPLE 21

To a mixture of 3-(2-aminoethyl)thiomethyl-7-chloro-2-methylimidazo[2,1-a]isoquinoline (1.5 g) and triethylamine (0.5 g) in ethyl alcohol (35 ml) was added portionwise 3-chloro-1,2-benzisothiazole-1,1dioxide (1.0 g). After being stirred at ambient temperature for 1 hour, the resulting precipitate was collected by filtration and washed several times with ethyl alcohol to give 3-[2-[(7-chloro-2-methylimidazo[2,1-a]isoquinolin-3-yl)methylthio]ethylamino]-1,2-benzisothiazole-1,1-dioxide (2.2 g).

mp: 291° to 294° C. (dec.)

IR (Nujol): 3300, 1615, 1580 cm$^{-1}$

NMR (DMSO-d$_6$, δ): 2.43 (3H, s), 2.77 (2H, t, J=7 Hz), 3.63 (2H, m), 4.3 (2H, s), 7.27–8.50 (9H, m), 9.4 (1H, t, J=6 Hz)

EXAMPLE 22

To a solution of 7-chloro-2-methyl-3-methylthiomethylimidazo[2,1-a]isoquinoline (2 g) in chloroform (20 ml) was added portionwise 70% m-chloroperbenzoic acid (1.78 g). After being stirred under ice cooling for 30 minutes, the mixture was washed successively with aqueous sodium bicarbonate, water and brine, dried over magnesium sulfate, treated with activated charcoal and evaporated in vacuo. The residue was purified by column chromatography on silica gel (25 g) with a mixture of chloroform and methanol (50:1) as an eluent to afford a solid. This solid was recrystallized from ethanol to give 7-chloro-2-methyl-3-methylsulfinylmethylimidazo[2,1-a]isoquinoline (1.36 g).

mp: 205° to 207° C. (dec.)

IR (Nujol): 1595, 1560, 1500, 1365, 1055, 1025 cm$^{-1}$

NMR (DMSO-d$_6$, δ): 2.42 (3H, s), 2.58 (3H, s), 4.41 (1H, d, J=15 Hz), 4.77 (1H, d, J=15 Hz), 7.27–7.83 (3H, m), 8.30–8.62 (2H, m)

EXAMPLE 23

To a solution of 7-chloro-2-methyl-3-methylthiomethylimidazo[2,1-a]isoquinoline (2 g) in chloroform (40 ml) was added 70% m-chloroperbenzoic acid (3.74 g) under ice-cooling and then the mixture was stirred for 1 hour at room temperature. The mixture was washed successively with aqueous sodium carbonate and water, dried over magnesium sulfate, treated with activated charcoal and evaporated in vacuo. The residue was recrystallized from a mixture of chloroform and methanol to give 7-chloro-2-methyl-3-methylsulfonylmethylimidazo[2,1-a]isoquinoline (1.17 g).

IR (Nujol): 1560, 1500, 1310, 1120 cm$^{-1}$

NMR (CF$_3$COOH, δ): 2.82 (3H, s), 3.47 (3H, s), 5.18 (2H, s), 7.75–8.70 (5H, m)

EXAMPLE 24

A mixture of 7-chloro-3-cyanomethyl-2-methylimidazo[2,1-a]isoquinoline (6 g) in a saturated solution of hydrogen chloride in ethanol (80 ml) was refluxed for 5 hours and evaporated in vacuo. To the residue was added aqueous sodium bicarbonate and extracted with chloroform. The extract was washed with brine, dried over magnesium sulfate and evaporated in vacuo. The crystalline residue was recrystallized from ethyl acetate to give 7-chloro-3-ethoxycarbonylmethyl-2-methylimidazo[2,1-a]isoquinoline (6.1 g).

mp: 137° to 138° C.

IR (Nujol): 1715, 1590, 1565, 1195 cm$^{-1}$

NMR (CF$_3$COOH, δ): 1.42 (3H, t, J=7 Hz), 2.68 (3H, s), 4.32 (2H, s), 4.43 (2H, q, J=7 Hz), 7.72–8.60 (5H, m)

EXAMPLE 25

A solution of sodium hydroxide (1.25 g) in water (5 ml) was added to a mixture of 7-chloro-3-ethoxycarbonylmethyl-2-methylimidazo[2,1-a]isoquinoline (4.75 g) and methanol (48 ml) and the mixture was refluxed for 1.5 hours. After being cooled, the mixture was evaporated in vacuo and 1N hydrochloric acid (31.4 ml) was added to the residue under ice-cooling. The resulting precipitate was collected by filtration, washed with water, dried in a desiccator and washed with a mixture of ethanol and methanol to give 3-carboxymethyl-7-chloro-2-methylimidazo[2,1-a]isoquinoline (3.2 g).

mp: 275° to 276° C. (dec.)
IR (Nujol): 1690, 1585, 1500 cm$^{-1}$
NMR (CF$_3$COOH, δ): 2.68 (3H, s), 4.32 (2H, s), 7.70–8.57 (5H, m)

EXAMPLE 26

The following compound was obtained according to a similar manner to that of Example 25.

3-Carboxy-7-chloro-2-methylimidazo[2,1-a]isoquinoline mp: 228° to 230° C. (dec.)
IR (Nujol): 2450, 1680, 1495 cm$^{-1}$
NMR (CF$_3$COOH, δ): 2.07 (3H, s), 7.77–8.63 (4H, m), 9.47 (1H, d, J=7.5 Hz)

EXAMPLE 27

A mixture of 3-carboxy-7-chloro-2-methylimidazo[2,1-a]isoquinoline (2.5 g) and thionyl chloride (20 ml) was refluxed for 1 hour and evaporated in vacuo. The residual solid was washed with benzene and dried in a desiccator to give 7-chloro-3-chloroformyl-2-methylimidazo[2,1-a]isoquinoline hydrochloride (2.75 g).

IR (Nujol): 1790 cm$^{-1}$

EXAMPLE 28

To 28% ammonium hydroxide (50 ml) was added 7-chloro-3-chloroformyl-2-methylimidazo[2,1-a]isoquinoline hydrochloride (1.3 g) and the mixture was stirred under ice-cooling for 40 minutes. The resulting precipitate was collected by filtration, washed with water and recrystallized from a mixture of chloroform and methanol to give 3-carbamoyl-7-chloro-2-methylimidazo[2,1-a]isoquinoline (0.75 g).

mp: 289° to 290° C. (dec.)
IR (Nujol): 3340, 3160, 1630, 1595 cm$^{-1}$
NMR (CF$_3$COOH, δ): 3.00 (3H, s), 7.33–7.73 (2H, m), 7.73–7.93 (4H, m), 9.20 (1H, d, J=8 Hz)

EXAMPLE 29

Thionyl chloride (0.56 ml) was added dropwise to a suspension of 3-carboxymethyl-7-chloro-2-methylimidazo[2,1-a]isoquinoline (0.855 g) in methylene chloride (9 ml) and the mixture was stirred for 2 hours at room temperature. The resulting precipitate was collected by filtration, washed with methylene chloride and then treated with 28% ammonium hydroxide (20 ml) for 1 hour. The resulting precipitate was collected by filtration, washed with water and recrystallized from ethanol to give 3-carbamoylmethyl-7-chloro-2-methylimidazo[2,1-a]isoquinoline (0.75 g).

mp: 284° to 286° C.
IR (Nujol): 3350, 3100, 1665, 1610, 1510 cm$^{-1}$
NMR (CF$_3$COOH, δ): 2.73 (3H, s), 4.3 (2H, s), 7.73–8.57 (5H, m)

EXAMPLE 30

The following compound was obtained according to a similar manner to that of Example 29. 2-(7-Chloro-2-methylimidazo[2,1-a]isoquinolin-3-yl)acetohydroxamic acid mp: 249° to 254° C. (dec.)
IR (Nujol): 3200, 1645, 1410 cm$^{-1}$
NMR (CF$_3$COOH, δ): 2.73 (3H, s), 4.33 (2H, s), 7.7–8.7 (5H, m)

EXAMPLE 31

Lithium aluminum hydride (0.668 g) was added portionwise to a solution of 7-chloro-3-ethoxycarbonyl-(2-methylimidazo[2,1-a]isoquinoline (5.1 g) in tetrahydrofuran (100 ml) with ice-cooling under nitrogen atmosphere and the mixture was stirred at room temperature for 1.5 hours. After an addition of ethyl acetate, the mixture was evaporated in vacuo and the residue was extracted with hot ethanol. The extract was treated with activated charcoal and evaporated in vacuo. The residue was recrystallized from 90% ethanol to give 7-chloro-3-hydroxymethyl-2-methylimidazo[2,1-a]isoquinoline (1.94 g).

mp: 231° to 232° C.
IR (Nujol): 3120, 1570, 1500 cm$^{-1}$
NMR (CF$_3$COOH, δ): 2.75 (3H, s), 5.40 (2H, s), 7.87–8.70 (5H, m)

EXAMPLE 32

Acetic anhydride (0.71 g) was added dropwise to a suspension of 7-chloro-3-hydroxymethyl-2-methylimidazo[2,1-a]isoquinoline (1.43 g) in pyridine (14 ml) and the mixture was stirred at room temperature for 24 hours. The mixture was evaporated in vacuo and the residue was extracted with chloroform after an addition of water to it. The extract was washed with water, dried over magnesium sulfate, treated with activated charcoal and evaporated in vacuo. The crystalline residue was recrystallized from a mixture of ethyl acetate and diisopropyl ether to give 3-acetoxymethyl-7-chloro-2-methylimidazo[2,1-a]isoquinoline (0.6 g).

mp: 137° to 139° C.
IR (Nujol): 1730, 1570, 1510 cm$^{-1}$
NMR (CDCl$_3$, δ): 2.07 (3H, s), 2.53 (3H, s), 5.40 (2H, s), 7.23–7.75 (3H, m), 8.00 (1H, d, J=7 Hz), 8.50 (1H, dd, J=6.5, 2.5 Hz)

EXAMPLE 33

A mixture of 1-amino-5-chloroisoquinoline (6.1 g), ethyl 2-acetyl-2-bromoacetate (10.75 g) and sodium bicarbonate (14.36 g) in ethanol (72 ml) was refluxed for 2 hours and then filtered by suction. The filtrate was evaporated in vacuo, and the residue was dissolved in a mixture of chloroform and methanol. The solution was treated with silica gel (10 g) and filtered by suction. The filtrate was evaporated in vacuo and the residue was recrystallized from ethanol to give 7-chloro-3-ethoxycarbonyl-2-methylimidazo[2,1-a]isoquinoline (5.83 g).

mp: 140° to 141° C.
IR (Nujol): 1690, 1415, 1260, 1190, 1100 cm$^{-1}$
NMR (CDCl$_3$, δ): 1.46 (3H, t, J=7 Hz), 2.73 (3H, s), 4.40 (2H, q, J=7 Hz), 7.20–7.73 (3H, m), 8.43 (1H, dd, J=7 Hz, 2.5 Hz), 8.93 (1H, d, J=7.5 Hz)

EXAMPLE 34

To a suspension of 1-amino-5-chloroisoquinoline (10 g) in chloroform (150 ml) was added dropwise 3-chloro-2,4-pentanedione (11.3 g). The mixture was refluxed for 6 hours and then allowed to stand at room temperature over night. The mixture was washed successively with aqueous sodium bicarbonate and water, dried over magnesium sulfate and evaporated in vacuo. The residue was purified by column chromatography on silica gel (200 g) with chloroform as an eluent to afford a solid. This solid was recrystallized from ethyl acetate to give 3-acetyl-7-chloro-2-methylimidazo[2,1-a]isoquinoline (1.3 g).

IR (Nujol): 1630, 1500 cm$^{-1}$
NMR (CF$_3$COOH, δ): 2.97 (3H, s), 3.15 (3H, s), 7.82–8.72 (4H, m), 9.76 (1H, d, J=7.5 Hz)

EXAMPLE 35

The following compound was obtained according to similar manners to those of Examples 33 and 34.

7-Chloro-2,3-dimethylimidazo[2,1-a]isoquinoline mp: 167° to 169° C.
IR (Nujol): 1595, 1568, 1505 cm$^{-1}$
NMR (CF$_3$COOH, δ): 2.67 (6H, s), 7.7–8.6 (5H, m)

What we claim is:
1. A compound of the formula:

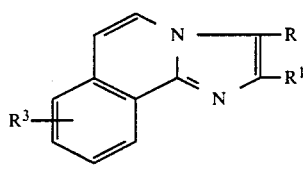

wherein R$^1$ is lower alkyl,
R$^3$ is hydrogen, halogen or phenyl(lower)alkoxy, and
R is lower alkanoyl, nitroso, amino, carboxy, lower alkoxycarbonyl, carbamoyl, hydroxycarbamoyl, haloformyl, aminomethyleneamino which may be substituted with cyano or lower alkyl, iminomethylamino which may be substituted with cyano or lower alkyl, or a group of the formula: —A—R$^2$ in which
A is lower alkylene and
R$^2$ is di(lower)alkylamino, cyano, lower alkoxy, lower alkynyloxy, lower alkenyloxy, lower alkylthio, amino(lower)alkylthio, lower alkylsulfinyl, lower alkylsulfonyl, carboxy, lower alkoxycarbonyl, carbamoyl, hydroxycarbamoyl, hydroxy, lower alkanoyloxy, hydrogen or a group of the formula:

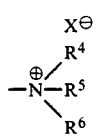

in which
R$^4$, R$^5$ and R$^6$ are each lower alkyl and
X is an acid residue,
and pharmaceutically acceptable salts thereof.

2. A compound of claim 1, wherein
R$^3$ is hydrogen, halogen or phenyl(lower)alkoxy, and
R is lower alkanoyl, nitroso, amino, carboxy, lower alkoxy carbonyl, carbamoyl, hydroxycarbamoyl, haloformyl, cyanoaminomethyleneamino, lower alkylaminomethyleneamino, cyanoiminomethylamino, lower alkyliminomethylamino, or a group of the formula: —A—R$^2$ in which
A is lower alkylene and
R$^2$ is di(lower)alkylamino, cyano, lower alkoxy, lower alkynyloxy, lower alkenyloxy, lower alkylthio, amino(lower)alkylthio, lower alkylsulfinyl, lower alkylsulfonyl, carboxy, lower alkoxy carbonyl, carbamoyl, hydroxycarbamoyl, hydroxy, lower alkanoyloxy, hydrogen or a group of the formula:

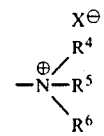

in which R$^4$, R$^5$ and R$^6$ are each lower alkyl,
X is an acid residue.

3. A compound of claim 2, wherein
R is lower alkanoyl, nitroso, amino, carboxy, lower alkoxycarbonyl, carbamoyl, hydroxycarbamoyl, haloformyl, cyanoaminomethyleneamino, lower alkylaminomethyleneamino, cyanoiminomethylamino, lower alkyliminomethylamino, or a group of the formula: —A—R$^2$ in which
A is lower alkylene and
R$^2$ is di(lower)alkylamino, cyano, lower alkoxy, lower alkynyloxy, lower alkenyloxy, lower alkylthio, amino(lower)alkylthio, lower alkylsulfinyl, lower alkylsulfonyl, carboxy, lower alkoxycarbonyl, carbamoyl, hydroxycarbamoyl, hydroxy, lower alkanoyloxy, hydrogen or a group of the formula:

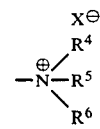

in which
R$^4$, R$^5$ and R$^6$ are each lower alkyl,
X is residue of lower alkylsulfuric acid, or halogen.

4. A compound of claim 3, wherein
R$^3$ is halogen, and
R is a group of the formula:

in which
A is lower alkylene and
R$^2$ is cyano.

5. A compound of claim 4, which is 7-chloro-3-cyanomethyl-2-methylimidazo[2,1-a]isoquinoline.

6. An anti-ulcer composition comprising an amount of a compound of claim 1 or pharmaceutically acceptable salt thereof such that it will provide an antiulceratively effective amount of said compound when administered to a warm blooded animal in association with a pharmaceutically acceptable, substantially non-toxic carrier or excipient.

7. The composition of claim 6 wherein said effective amount is 1 to 6,000 mg/day.

8. A method of inhibiting ulcers comprising administering an antiulceratively effective amount of a compound of claim 1 to a warm blooded animal.

9. The method of claim 8 wherein said effective amount is 1 to 6,000 mg/day.

* * * * *